United States Patent
Manz et al.

(10) Patent No.: US 8,632,733 B2
(45) Date of Patent: Jan. 21, 2014

(54) DEVICE AND KIT FOR COLLECTING BODY FLUIDS

(75) Inventors: Bernhard Manz, Nordhorn (DE); Matthias Kuper, Wietmarschen (DE)

(73) Assignee: Labor Diagnostika Nord GmbH & Co. KG, Nordhorn (DE)

( * ) Notice: Subject to any disclaimer, the term of this patent is extended or adjusted under 35 U.S.C. 154(b) by 214 days.

(21) Appl. No.: 12/931,020

(22) Filed: Jan. 21, 2011

(65) Prior Publication Data

US 2011/0190663 A1 Aug. 4, 2011

Related U.S. Application Data

(60) Provisional application No. 61/336,515, filed on Jan. 22, 2010.

(51) Int. Cl.
| | |
|---|---|
| *G01N 21/75* | (2006.01) |
| *G01N 31/22* | (2006.01) |
| *G01N 33/52* | (2006.01) |
| *C12Q 1/68* | (2006.01) |
| *A61B 5/00* | (2006.01) |
| *B65D 81/00* | (2006.01) |
| *A61F 13/15* | (2006.01) |
| *A61F 13/20* | (2006.01) |

(52) U.S. Cl.
USPC ............ 422/409; 422/50; 422/401; 422/408; 600/573; 604/358; 604/385.01; 604/385.201

(58) Field of Classification Search
USPC ............. 600/573; 422/409; 604/358, 385.01, 604/385.201
See application file for complete search history.

(56) References Cited

U.S. PATENT DOCUMENTS

| | | | |
|---|---|---|---|
| 5,520,041 A | * | 5/1996 | Haswell .................. 73/29.04 |
| 7,488,450 B2 | * | 2/2009 | Matusewicz et al. ......... 422/412 |
| 2003/0113906 A1 | | 6/2003 | Sangha et al. |

(Continued)

FOREIGN PATENT DOCUMENTS

| | | |
|---|---|---|
| WO | WO 02/31465 A1 | 4/2002 |
| WO | WO 2004/081514 A2 | 9/2004 |

*Primary Examiner* — Brian Szmal
*Assistant Examiner* — Megan Leedy
(74) *Attorney, Agent, or Firm* — Olson & Cepuritis, Ltd.

(57) ABSTRACT

The present invention provides for a device and a kit for collecting body fluids. The device includes a body fluid collection portion comprising a body fluid absorbing material. The body fluid connecting portion has a free edge and is hingedly connected at the edge opposite to the free edge to a first support panel and a second support panel. A base panel is hingedly connected to the first support panel or the second support panel. In a first folded condition the body fluid collection portion is sandwiched between the first support panel and the second support panel in a substantially face contacting relationship. The device for collecting body fluids is configured to be folded from the first folded condition into a second folded condition, wherein the body fluid collection portion is exposed so that by grasping the device for collecting body fluids by means of a handle formed by the first support panel, the second support panel and optionally the base panel the body fluid collection portion can be inserted into a sample container containing a body fluid to be sampled. Moreover, the device for collecting body fluids is configured to be folded from the second folded condition into a drying or triangle configuration, wherein the first support panel, the second support panel and the base panel form the three sides of a triangle such that the body fluid collection portion is suspended from its hinged connection with the first and second support panels and arranged within the space defined by the first and second support panels and the base panel.

12 Claims, 3 Drawing Sheets

(56) References Cited

U.S. PATENT DOCUMENTS

| | | |
|---|---|---|
| 2004/0071594 A1 | 4/2004 | Malone et al. |
| 2004/0171173 A1 | 9/2004 | Eckermann et al. |
| 2005/0220677 A1 | 10/2005 | Sangha |
| 2005/0263420 A1 | 12/2005 | Oommen |
| 2006/0147944 A1* | 7/2006 | Chomczynski .................. 435/6 |
| 2008/0299010 A1* | 12/2008 | Shivji ........................... 422/102 |

* cited by examiner

DEVICE AND KIT FOR COLLECTING BODY FLUIDS

CROSS REFERENCE TO RELATED APPLICATION

This application claims the benefit of U.S. Provisional Application No. 61/336,515, filed Jan. 22, 2010, which is incorporated herein by reference.

FIELD OF THE INVENTION

Generally, the present invention relates to a device and a kit for collecting body fluids. In particular, the present invention relates to such a device and kit for collecting a urine or saliva sample.

BACKGROUND OF THE INVENTION

Urine and saliva tests are very useful for providing information about the bodies hormonal or nutritional balance or dysbalance and to assist in the diagnosis, monitoring and treatment of a wide range of diseases. In addition, a urine test can determine whether or not a woman is ovulating or pregnant. Urine and saliva can also be tested for a variety of substances relating to drug abuse, both as part of rehabilitation programmes and in the world of professional sport. The urine and saliva can be tested very quickly using a strip of special paper, which is dipped in the urine just after urination or wet with saliva. This is because any abnormally elevated or low levels of hormones or nutrients and their respective metabolites or drugs and their respective metabolites in the urine or saliva such as neurotransmitters, hormones or amino acids will be observable.

By means of an analysis of a urine or saliva sample at a laboratory, i.e. a urine or saliva test, it is possible to discover diseases or dysfunctions of many different organs of the body. It may represent the only necessary investigation if, for instance, the purpose is to find out if a patient suffers from cystitis. In other cases it will be taken along with other tests (such as stool or blood tests) as part of the investigation process. A urine or saliva test is a cheap, simple test that can provide a lot of important information, for example: blood in the urine may be a sign of different diseases in the kidneys, the urinary system or the bladder; sugar in the urine may be a sign of diabetes; protein in the urine may be a sign of a kidney disease and can be used to detect the early signs of kidney damage from long-standing diabetes; biochemical analysis of the urine can assist in the diagnosis of kidney stones, myeloma and porphyria. High Cortisol levels in saliva may be a sign for permanent stress and high Histamine levels may indicate parodontitis.

Usually a person, who wants to do have a urine or saliva test made, visits a doctor or a clinic where a sample of urine or saliva is taken by means of a sterile sample container. After the sample container has been filled with a sufficient amount of urine or saliva, the sample container is sealed and brought to a laboratory for analysis. Thus, the conventional process of having a urine or saliva test made is time consuming and cumbersome in that it is necessary for a patient to visit a doctor or a clinic. Although it is also possible to take a urine or saliva sample at home, the filled sample container still has to be supplied to a laboratory so that this alternative is no less cumbersome. In addition, precautions need to be taken to avoid decomposition of sensitive hormones during the transport to the laboratory, especially if ambient temperature is high, i.e. in summer, or if the transport time is critical.

Consequently, the object of the present invention is to provide a device and a kit for collecting body fluids that allow for an easy to use, comfortable and clean urine or saliva test to be made.

SUMMARY OF THE INVENTION

According to a first aspect of the invention a device for collecting body fluids is provided. The device includes a body fluid collection portion comprising a body fluid absorbing material. The body fluid connecting portion has a free edge and is hingedly connected at the edge opposite to the free edge to a first support panel and a second support panel. A base panel is hingedly connected to the first support panel or the second support panel.

In a first folded condition the body fluid collection portion is sandwiched between the first support panel and the second support panel in a substantially face contacting relationship. The device for collecting body fluids is configured to be folded from the first folded condition into a second folded condition, wherein the body fluid collection portion is exposed so that by grasping the device for collecting body fluids by means of a handle formed by the first support panel, the second support panel and optionally the base panel the body fluid collection portion can be inserted into a sample container containing a body fluid to be sampled. Moreover, the device for collecting body fluids is configured to be folded from the second folded condition into a triangle configuration, wherein the first support panel, the second support panel and the base panel form the three sides of a triangle such that the body fluid collection portion is suspended from its hinged connection with the first and second support panels and arranged within the space defined and surrounded by the first and second support panels and the base panel without substantially contacting these panels.

Preferably, the body fluid collection portion comprises at least one body fluid collection panel made from a body fluid absorbing material and a solid support panel.

Preferably, the width W and the length L and of the body fluid collection panel are smaller than the respective widths and lengths of the first and second support panels and the base panel.

According to a second aspect of the invention a kit for collecting body fluids is provided comprising a device for collecting body fluids according to the first aspect of the invention.

Additional advantages and features of the present invention will become apparent by reference to the following detailed description and accompanying drawings.

DETAILED DESCRIPTION OF PREFERRED EMBODIMENTS

The present invention will now be further described by defining different aspects of the invention generally outlined above in more detail. Each aspect so defined may be combined with any other aspect or aspects unless clearly indicated to the contrary. In particular, any feature indicated as being preferred or advantageous may be combined with any other feature or features indicated as being preferred or advantageous.

Figure 1:
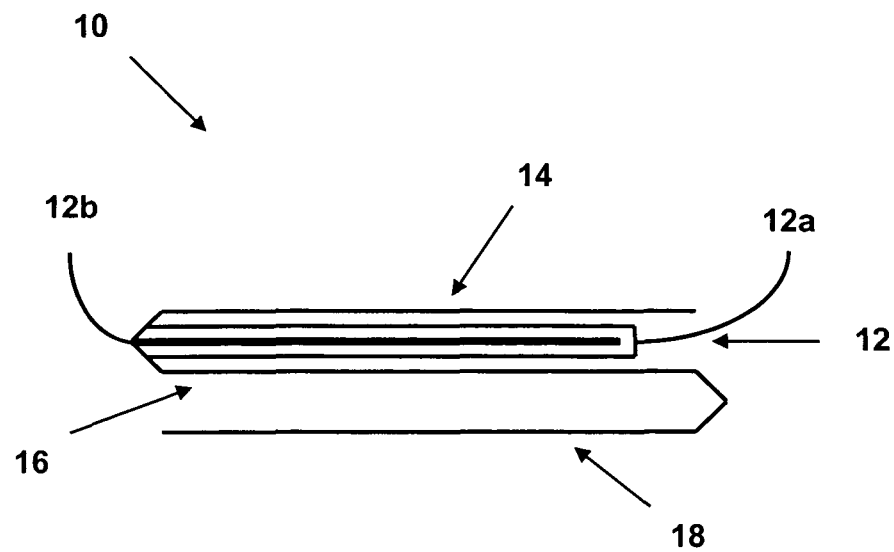
FIG. 1 shows a schematic side view of a device for collecting body fluids according to a preferred embodiment of the invention in a first folded condition, as it would be supplied to a user or customer.
Figure 2:
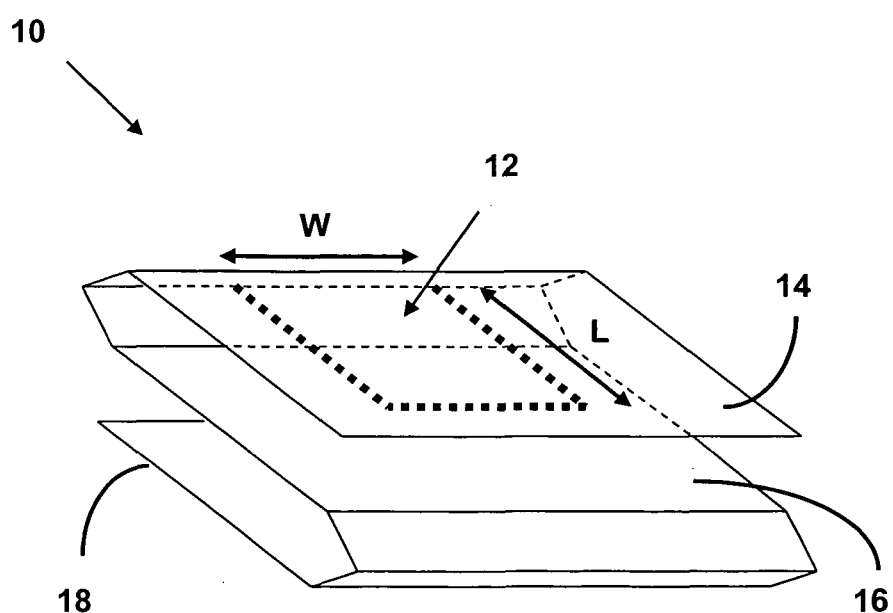
FIG. 2 shows a schematic perspective view of a device for collecting body fluids according to a preferred embodiment of the invention in a first folded condition, as it would be supplied to a user or customer.

FIGS. 1 and 2 show schematically a side view and a perspective view of a device 10 for collecting body fluids according to a preferred embodiment of the invention in a first folded condition, as it could be supplied to a user. Preferably, the overall shape of this device 10 in the first folded condition is similar to the shape and size of a credit card, i.e. rectangular and flat. Preferred dimensions of the device 10 for collecting body fluids in the first folded condition shown in FIGS. 1 and 2 are a length of less than about 10 cm and a width of less than about 6 cm.

The device 10 for collecting body fluids comprises a body fluid collection portion 12. According to the preferred embodiment of the device 10 shown in FIGS. 1 and 2 the body fluid collection portion 12 comprises at least one body fluid collection panel 12a made from a fluid absorbing material, such as fluid absorbing paper, and a support panel 12b made from a solid material, such as plastic. As can be taken from FIG. 1, the support panel 12b is sandwiched between two halves of the body fluid collection panel 12a that are connected via a hinged connection, such as a fold line, at the free edge of the support panel 12b.

The body fluid collection portion 12 is at one end thereof hingedly connected to a first support panel 14 and a second support panel 16 such that in the first folded condition shown in FIGS. 1 and 2 the body fluid collection portion 12 is sandwiched between the first support panel 14 and the second support panel 16 in a substantially face contacting relationship. The second support panel 16, in turn, is hingedly connected to a base panel 18. According to a preferred embodiment the first support panel 14, the second support panel 16 and the base panel 18 have substantially similar dimensions. As can be taken from FIG. 2, the width W and the length L of the body fluid collection portion 12 are preferably smaller that the corresponding widths and lengths of the first support panel 14 and the second support panel 16 for reasons that will be described in more detail further below.

Figure 3:
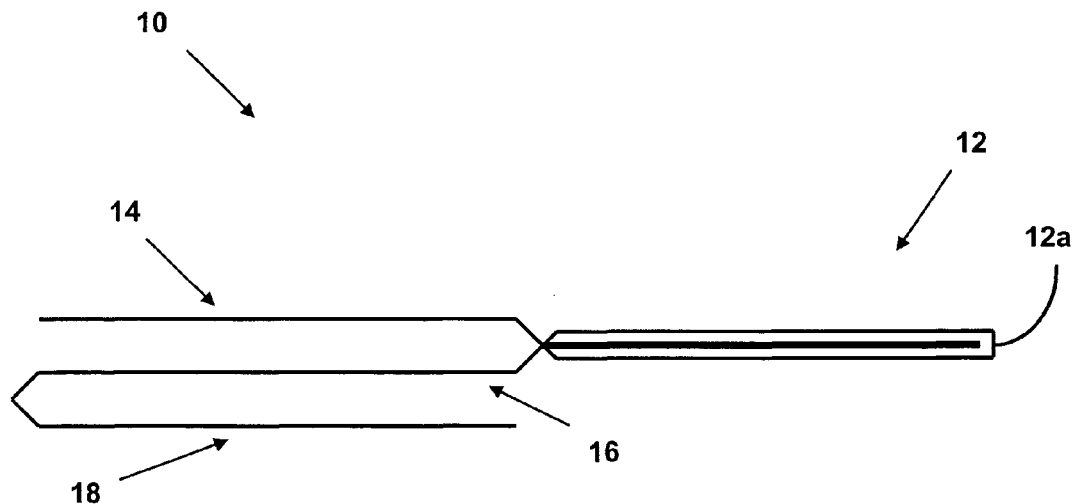
FIG. 3 shows a schematic side view of the device for collecting body fluids of FIGS. 1 and 2 in a second folded condition, wherein a body fluid collection portion is exposed for insertion into a sample container.

The device 10 for collecting body fluids according to the described preferred embodiment is configured to be easily brought from the first folded condition shown in FIGS. 1 and 2 into a second folded condition shown in FIG. 3 by a simple folding operation. The first support panel 14 is folded along the hinged connection with the body fluid collection portion 12, such as a fold line, by 180 degrees relative thereto. Likewise, the second support panel 16 is folded along the hinged connection with the body fluid collection portion 12 by 180 degrees relative thereto. And optionally, the base panel 18 can be folded along the hinged connection with the second support panel 16 by 180 degrees relative thereto. As can be taken from FIG. 3, by means of this simple folding operation the body fluid portion 12 is no longer sandwiched between the first support panel 14 and the second support panel 16. Rather the body fluid collection portion 12 now is exposed so that by grasping the device 10 for collecting body fluids by the "handle" formed by the first support panel 14, the second support panel 16 and optionally the base panel 18 the body fluid collection portion 12 can be inserted into a sample container containing a body fluid to be sampled, such as urine or saliva. Once inserted into the sample in the sample container, the body fluid collection panel 12a made from a fluid absorbing material, such as fluid absorbing paper, absorbs sample fluid. In doing so, the body fluid collection panel 12a substantially does not change its shape or size, by getting wrinkled or shrinking, because it is supported by the support panel 12b made from a solid material, such as solid plastic.

After an appropriate amount of sample fluid has been absorbed by the body fluid collection portion 12 or rather its body fluid collection panel 12a the body fluid collection portion 12 can be removed from the sample container by means of the "handle" formed by the first support panel 14, the second support panel 16 and optionally the base panel 18. Preferably, the body fluid collection panel 12a comprises substances and/or compositions that allow for a chemical stabilization of the body fluid absorbed by the body fluid collection panel 12a. For instance, in the case of an urine sample the body fluid collection panel 12a preferably comprises antioxidant agents, such as ascorbic acid, glutathion, sodium metabisulfit and/or chelate agents, such as ethylenediaminetetraacetic acid (EDTA) or dimercaptosuccinylic acid (DMSA).

Figure 4:
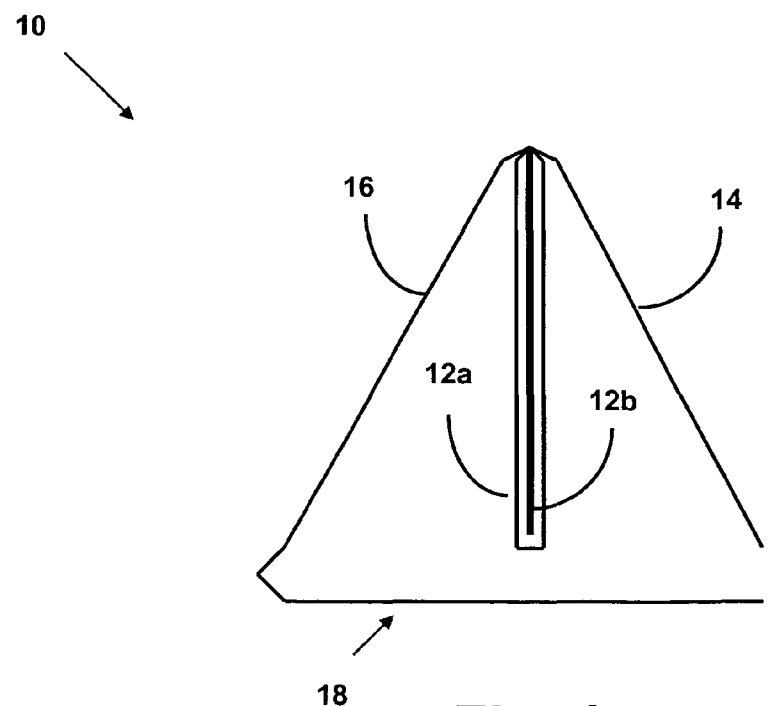
FIG. 4 shows a schematic side view of the device for collecting body fluids of FIGS. 1 and 2 in a substantially unfolded drying condition.

To support the drying and stabilizing process the device 10 for collecting body fluids according to the described preferred embodiment is configured to be easily brought from the second folded condition shown in FIG. 3 by means of another simple folding operation into a drying configuration having a triangular shape like that shown in FIG. 4. The first support panel 14 and the second support panel 16 are folded along the hinged connection with the body fluid collection portion 12 and the base panel 18 is folded along the hinged connection with the second support panel 16 such that the first support panel 14, the second support panel 16 and the base panel 18 form the three sides of a triangle. As can be taken from FIG. 4, this drying or triangle configuration allows the body fluid collection portion 12 to be suspended from its hinged connection with the first and second support panels 14, 16 and to be disposed in the space defined by the first and second support panels 14, 16 and the base panel 18. As the person skilled in the art will appreciate, in the drying or triangle configuration the body fluid collection portion 12 is no longer in a face-contacting relationship with the first and second support panels 14, but essentially free from the first and second support panels 14, 16 and the base panel 18 (except its hinged connection with the first and second support panels 14, 16). Preferably, the respective dimensions of the body fluid collection portion 12 and the first support panel 14, the second support panel 16 and the base panel 18 are such that in the drying or triangle configuration practically no external sunlight can reach the body fluid collection portion 12. This is important in order to protect any hormones, such as serotonin, contained in the sample absorbed by the fluid collection portion 12, which degrade quickly when exposed to direct sunlight.

In order to stabilize the drying or triangle configuration formed by the first support panel 14, the second support panel 16 and the base panel 18 the device 10 for collecting body fluids according to the described preferred embodiment furthermore can comprise fastening means for removably fastening the respective free ends of the first support panel 14 and the base panel 18 together. For instance, a fastening flap could be provided at the free end of the first support panel 14 for engaging a correspondingly shaped slit in the base panel 18 or vice versa.

Figure 5:
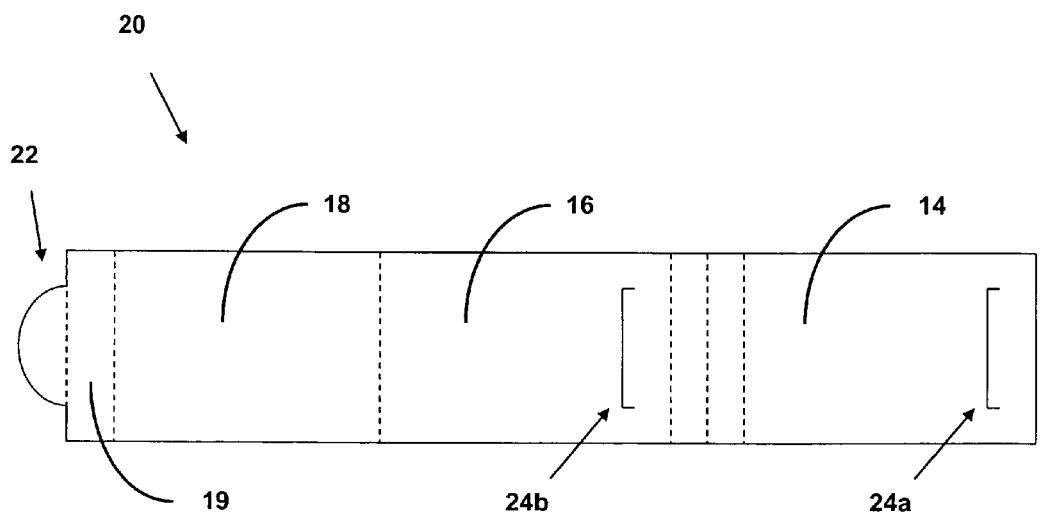
FIG. 5 shows a plan view of a blank for a device for collecting body fluids according to a further preferred embodiment of the present invention.

A blank 20 for forming a device 10 for collecting body fluids according to such a further preferred embodiment including fastening means is shown in FIG. 5. Besides the above described first support panel 14, second support panel 16 and base panel 18 that are hingedly connected together via fold lines (indicated by dashed lines) the blank 20 comprises a fastening flap 22 that is hingedly connected to an auxiliary panel 19, which, in turn, is hingedly connected to base panel 18. Moreover, corresponding slits 24a, 24b for receiving the fastening flap 22 are provided in the first and second support panels 14, 16, respectively. Preferably, the respective lengths of the different panels 14, 16, 18, 19 as well as the arrangement of the slits 24a, 24b provided in the first and second support panels 14, 16 are chosen such that in the drying or triangle configuration of the device 10 according to the present invention the fastening flap 22 can be inserted into the slit 24a provided in first support panel 14 and in the first folded condition, wherein the body fluid collection portion 12 is sandwiched between the first support panel 14 and the second support panel 18 in a substantially face contacting relationship, the fastening flap 22 can be inserted into the slit 24b provided in second support panel 16. With the fastening flap 22 being inserted in this way in the slit 24a or 24b the auxiliary panel 19 will be disposed in a substantially face-contacting relationship with a portion of the first support panel 14 (i.e. drying configuration) and a portion of the second support panel 16 (i.e. first folded condition), respectively. The person skilled in the art will readily appreciate that for inserting the fastening flap 22 into the slit 24b provided in the second support panel 16, i.e. for arranging the device 10 for collecting body fluids according to the present invention in the first condition, wherein the body fluid collection portion 12 is sandwiched between the first support panel 14 and the second support panel 18 in a substantially face contacting relationship, the base panel 18 has to be folded differently with respect to the second support panel to what is illustrated in FIGS. 1 and 2. Because for inserting the fastening flap 22 into the slit 24b provided in the second support panel 16 the base panel 18 has to be folded so that it comes into a face-contacting relationship with the first support panel 14 and not with the second support panel 16, shown for a different embodiment in FIGS. 1 and 2.

Figure 6:
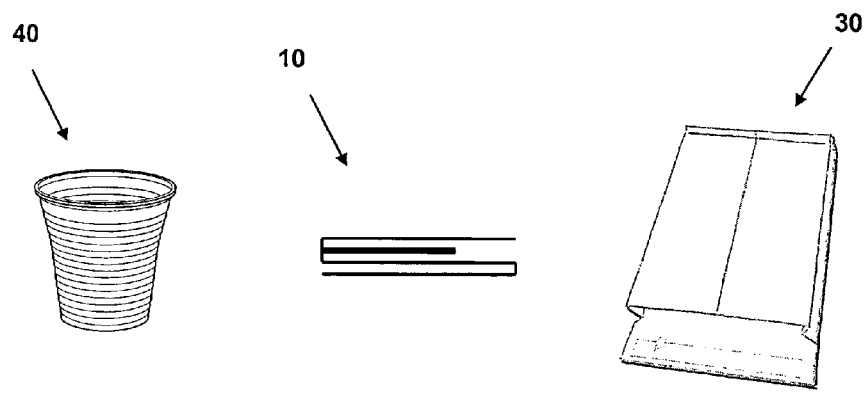
FIG. 6 shows schematically the components of a kit containing a device for collecting body fluids according to the present invention.

After the sample absorbed by the body fluid collection panel 12a has completely dried and, if present, the fastening means have been disengaged, such as the above described fastening flap 22 and the correspondingly shaped slits 24a, 24b, the device 10 for collecting body fluids according to the present invention is configured to be easily brought from the drying or triangle configuration shown in FIG. 4 back into the first folded condition shown in FIGS. 1 and 2 by appropriately folding the first support panel 14 and the second support panel 16 along the hinged connection with the body fluid collection portion 12 onto body fluid collection portion 12 and into a face contacting relationship therewith and, likewise, by folding the base panel 18 along the hinged connection with the second support panel 16 either onto the first support panel 14 and into a face contacting relationship therewith (as would be the case for the blank 20 shown in FIG. 5) or onto the second support panel 16 and into a face contacting relationship therewith (as shown in FIGS. 1 and 2). Once the device 10 for collecting body fluids according to the described preferred embodiment has been folded back into the first folded condition, the device 10 can be inserted into a sleeve 30 for holding the device 10 and allowing the device 10 to be posted to a laboratory for testing. An appropriate posting sleeve 30 is shown as part of a kit for collecting body fluids in FIG. 6. The kit shown in FIG. 6 furthermore comprises a sample container 40 for initially collecting the body fluid to be tested and for inserting the body fluid collection portion 12 of the device 10 there into. The kit, moreover, can comprise a body fluid stabilizer to be applied to the fluid collection portion 12 and/or instructions for using the kit.

It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

While the foregoing description includes details which will enable those skilled in the art to practice the invention, it should be recognized that the description is illustrative in nature and that many modifications and variations thereof will be apparent to those skilled in the art having the benefit of these teachings. For instance, the body fluid collection portion 12 does not have to comprise a body fluid collection panel 12a and a support panel. For instance, for some body fluids it is conceivable that the body fluid collection portion 12 only comprises a body fluid collection panel that can absorb a sufficient amount of the body fluid, but does change its shape, when absorbing the body fluid. To this end, the body fluid collection panel could be made from paperboard instead of paper. Moreover, the absorbing portion of the body fluid collection portion does not have to be provided in the form of a panel. The present invention contemplates also other shapes and configurations. For instance, it is conceivable that a circular shaped absorbing panel is glued to a solid support panel or the absorbing portion could be provided in the form of a circular sponge-like material glued to a solid support panel. Finally, although the preferred embodiment has been described in the context of collecting a urine or saliva sample, the teachings of the present invention can be applied to other body fluids as well, such as blood and the like. It is accordingly intended that the invention herein be defined solely by the claims appended hereto and that the claims be interpreted as broadly as permitted.

The invention claimed is:

1. A device (10) for collecting body fluids, comprising:
   a body fluid collection portion (12) comprising a body fluid absorbing material;
   a first (14) and a second (16) support panel hingedly connected to the body fluid collection portion (12);
   and a base panel (18) hingedly connected to the first support panel (14) or the second support panel (16);
   wherein said first support panel, second support panel and base panel have similar dimensions and the device (10) is configured to be arranged:
   (i) in a first folded condition, wherein the body fluid collection portion (12) is sandwiched between the first support panel (14) and the second support panel (16) in a face contacting relationship;
   (ii) in a second folded condition, wherein the body fluid collection portion (12) is exposed and the first support panel (14) and the second support panel (16) define a handle so that by grasping the handle formed by the first support panel (14) and the second support panel (16) the body fluid collection portion (12) can be inserted into a sample container containing a body fluid to be sampled; and (iii) in a triangle configuration, wherein the first support panel (14), the second support panel (16) and the base panel (18) form the three sides of a triangle such that the body fluid collection portion (12) can be suspended above base panel (18) from its hinged connection with the first (14) and second (16) support panels and can be arranged in the space defined by the first and second support panels (14, 16) and the base panel (18).

2. The device (10) of claim 1, wherein the body fluid collection portion (12) comprises at least one body fluid collection panel (12a) made from a body fluid absorbing material and a solid support panel (12b).

3. The device (10) of claim 2, wherein the body fluid collection panel (12a) is made from fluid absorbing paper and the solid support panel (12b) is made from solid plastic.

4. The device (10) of claim 2, wherein the width (W) and the length (L) of the body fluid collection panel (12a) are smaller than the respective widths and lengths of the first and second support panels (14, 16) and the base panel (18).

5. The device (10) of claim 1, further comprising fastening means for removably fastening the device (10) in the first folded condition and/or the triangle configuration.

6. The device (10) of claim 5, wherein the fastening means comprise a fastening flap (22) for engaging a correspondingly shaped slit (24a, 24b) for fastening the device (10) in the first folded condition and/or the triangle configuration.

7. The device (10) of claim 1, wherein the body fluid collection portion (12) contains a substance that allows for a chemical stabilization of the body fluid.

8. The device (10) of claim 7, wherein said substance in the body fluid collection portion (12) is an antioxidant agent.

9. The device (10) of claim 7, wherein said substance in the body fluid collection portion (12) is a chelate agent.

10. A kit, comprising:
a device (10) for collecting body fluids according to claim 1; and
a sleeve (30) for receiving and holding the device (10) in the first folded condition.

11. The kit according to claim 10, further comprising a sample container (40) for collecting a fluid sample.

12. The kit according to claim 10, further comprising a body fluid stabilizer to be applied to the fluid collection portion (12) and/or instructions for using the kit.

* * * * *